(12) United States Patent
Rongen et al.

(10) Patent No.: US 7,877,132 B2
(45) Date of Patent: Jan. 25, 2011

(54) MEDICAL VIEWING SYSTEM AND METHOD FOR DETECTING AND ENHANCING STATIC STRUCTURES IN NOISY IMAGES USING MOTION OF THE IMAGE ACQUISITION MEANS

(75) Inventors: Peter Maria Johannes Rongen, Eindhoven (NL); Raoul Florent, Ville d'Avray (FR); Pierre Lelong, Nogent sur Marne (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 523 days.

(21) Appl. No.: 11/912,313

(22) PCT Filed: Apr. 13, 2006

(86) PCT No.: PCT/IB2006/051155
§ 371 (c)(1),
(2), (4) Date: Oct. 24, 2007

(87) PCT Pub. No.: WO2006/114721
PCT Pub. Date: Nov. 2, 2006

(65) Prior Publication Data
US 2008/0188739 A1    Aug. 7, 2008

(30) Foreign Application Priority Data
Apr. 26, 2005   (EP) .................................. 05103395

(51) Int. Cl.
*A61B 5/05* (2006.01)
(52) U.S. Cl. ......................... 600/424; 600/427; 382/128
(58) Field of Classification Search ................ 600/424, 600/427; 382/128–134, 254, 255
See application file for complete search history.

(56) References Cited

U.S. PATENT DOCUMENTS 5,841,830 A  *  11/1998  Barni et al. .................... 378/15
6,493,575 B1    12/2002  Kesten et al.
2003/0055410 A1  3/2003  Evans et al.

FOREIGN PATENT DOCUMENTS

EP    0860144 A2    8/1998

(Continued)

OTHER PUBLICATIONS

Irani et al: "Improving Resolution by Image Registration"; CVGIP: Graphical Models and Image Processing, vol. 53, No. 3, May 1991, pp. 231-239.

*Primary Examiner*—Long V Le
*Assistant Examiner*—Nicholas L Evoy (57) ABSTRACT

A method for use in a medical viewing system for processing for display a sequence of images of a medical intervention comprising manipulating a tool such as a stent (25) within an artery. Two markers (21, 22) are provided on the tool support (10) and the method includes extracting these markers (21, 22) to yield marker location information, from which tool location information can be derived. The image of the tool within the sequence of images is then enhanced relative to the background. The background can be additionally blurred by simulating or effecting relative movement of the image detector and the stent (25) by, for example, zooming in on the stent (25) or rotating the detector relative thereto, during acquisition of the sequence of images.

15 Claims, 5 Drawing Sheets

FOREIGN PATENT DOCUMENTS

| | | |
|---|---|---|
| WO | WO0202173 A1 | 1/2002 |
| WO | WO 03043516 A2 * | 5/2003 |
| WO | WO03043516 A2 | 5/2003 |
| WO | WO03045263 A2 | 6/2003 |
| WO | WO2004044847 A1 | 5/2004 |
| WO | WO2005029409 A2 | 3/2005 |

* cited by examiner

MEDICAL VIEWING SYSTEM AND METHOD FOR DETECTING AND ENHANCING STATIC STRUCTURES IN NOISY IMAGES USING MOTION OF THE IMAGE ACQUISITION MEANS

The invention relates to a medical viewing system for displaying a sequence of images of a medical intervention that comprises moving and/or positioning a tool in a body organ. The invention also relates to a computer-executable image processing method to be used in said system, and further to a medical examination apparatus coupled to such a system. The invention finds, for example, its application in the medical field of cardiology, for extracting, registering and enhancing thin objects of interest, such as stents.

It is of prime importance that a coronary stent is fully expanded after placement in a coronary stenotic lesion. However, a stent is not always clearly visible under fluoroscopy or in an exposure (cine) run. Improvement of stent visibility in X-ray exposure runs may thus assist the interventional cardiologist in judging the clinical success of an intervention.

A system and method for detecting and enhancing stents in medical images is known from U.S. Pat. No. 7,289,652 which describes an arrangement whereby a sequence of images is acquired and processed during a medical intervention so as to extract at least one radiopaque marker that is attached to the stent and provide marker location information, and thereby derive stent location information. Enhancing means may then be used to improve the visibility of the stent within the images. In another known system, such as that described in US 2006/0058643, registration means are provided for aligning markers in different image frames and the stent is then enhanced in these image frames whilst the background in the registered images is blurred. This blurring of the background is essentially possible due to the cardiac motion of the stent with respect to the static background. However, this enhancement technique is not so effective, and does not result in sufficiently blurred backgrounds in the images, in the case of static stents, for example, a carotid stent which is a slender metal-mesh tube which is inserted and then expanded in the carotid artery to increase blood flow in areas blocked by plaque.

It is therefore an object of the present invention to provide an improved medical viewing system and method for detecting and enhancing static structures, such as stents, in noisy images.

In accordance with the present invention, there is provided a method for use in a medical viewing system for processing for display a sequence of images of a medical intervention that comprises moving and/or positioning a tool in a body organ using a tool support, the method comprising the steps of acquiring by means of an image detector, a sequence of images of said tool during said medical intervention, during which acquisition step, movement of said image detector relative to said tool is effected or simulated, automatically extracting a marker attached to said tool support and yielding marker location information, deriving tool location information from said marker location information, and enhancing the images of said sequence to improve the visibility of said tool relative to the background.

Also in accordance with the present invention, there is provided a medical imaging system for displaying a sequence of images of a medical intervention that comprises moving and/or positioning a tool in a body organ, the system comprising an image detector for acquiring a sequence of images of said tool during said medical intervention, means for effecting or simulating movement of said image detector relative to said tool during acquisition of said sequence of images, means for processing said sequence of images according to the method defined above, and means for displaying said enhanced images.

Thus, relative movement between the detector and the tool is introduced during the acquisition of the sequence of images by effecting or simulating movement of the detector relative to the tool, by for example zooming in on the tool (which can be extended using so-called "super-resolution imaging") or rotating the detector relative to the patient in respect of which the medical intervention is being performed or the tool (beneficially substantially about a tool axis) so that an enhancement technique, such as that described above, can be effectively employed to display an enhanced image of even a static tool against a suitably blurred background. In the case where rotation of the detector is used to introduce the required relative motion, temporal recussive filtering means is preferably employed during the enhancement step to produce an image of a rotating enhanced tool.

Preferably, at least two markers are provided on the tool support. The method and system are particularly suited to medical interventions, wherein the tool is a stent and the body organ is an artery. In one exemplary embodiment, the tool may be stationary relative to the body organ during acquisition of the sequence of images.

In a preferred embodiment, the enhancement step includes a registration step to align respective markers in selected image frames of said sequence of images. The registration step beneficially includes one or more of translation, rotation, shifting, stretching, contracting or otherwise manipulating the tool in one of said selected image frames to align respective markers thereon with corresponding markers in another of said selected image frames.

Means are preferably provided for adjusting the playback speed of the sequence of images during display thereof in order to achieve a suitable view of, for example, a rotating stent. In the case where rotation of the detector relative to the tool is used to introduce the desired relative motion, the enhanced view of the tool may be back-projected in the image originally acquired, in order to achieve a normal view of the enhanced tool.

Beneficially, the method includes the step of receiving geometry system data for use during the image enhancement step. Again, in the case of the rotating detector, symmetrical temporal integration may be applied to image frames that are 180 degrees apart (and therefore contain the same projection of the tool), so as to improve the result of the enhancement step. This increases temporal integrations without decreasing spatial resolution. In a preferred embodiment, the window for temporal integration may be adapted to the rotation speed of the detector.

These and other aspects of the present invention will be apparent from, and elucidated with reference to, the embodiments described herein.

Embodiments of the present invention will now be described by way of examples only and with reference to the accompanying drawings, in which:

FIGS. 1a to 1d illustrate schematically respective registration steps to align balloon markers in selected image frames I and II of a stent sequence, wherein

The invention relates to a viewing system for detecting, localising, registering, enhancing and zooming structures in noisy images. The viewing system are described herein in an example of application to the medical field of cardiology. In the application, the objects of interest are organs such as arteries and tools such as balloons or stent. They are observed during a medical intervention called angioplasty, in a sequence of X-ray fluoroscopic images called angiograms. However, it will be appreciated that the system may be applied to other tools than stents and balloons in interventions other than angioplasties. For instance, the objects of interest may be electrodes and the organ may be the brain.

It is of prime importance that a coronary stent is fully expanded after placement in a coronary stenotic lesion. However, as explained above, a stent is not always clearly visible under fluoroscopy or in an exposure (cine) run. Improvement of stent visibility in X-ray exposure runs may thus assist the interventional cardiologist in judging the clinical success of an intervention. In a known system, a stent enhancement technique is employed to automatically enhance stent visibility, which technique is based on the automatic recognition of two radioopaque markers in all frames of an exposure. The markers are on the stent placement catheter. The catheter is kept in a steady position inside the stent immediately after stent expansion, and with deflated balloon, during the acquisition of an exposure run on a standard cardio X-ray system. After this, the catheter is removed and the run is transferred to a PC workstation running stent image enhancement software for off-line processing.

Figure 1A:
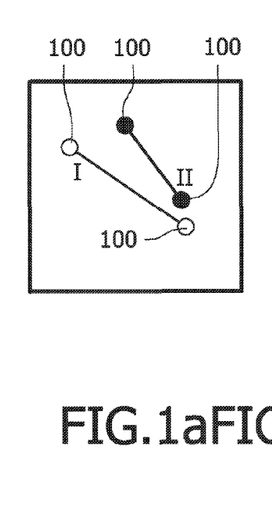
FIG. 1a illustrates automatic marker extraction in frames I and II.
Figure 1B:
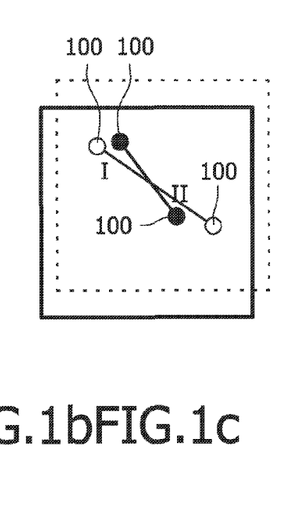
FIG. 1b illustrates a translation step.
Figure 1C:
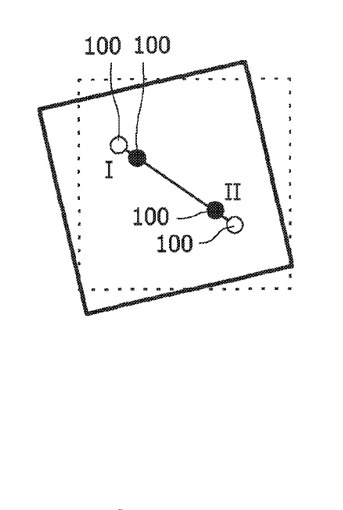
FIG. 1c illustrates a rotation step and FIG. 1d illustrates a stretching step.
Figure 1D:
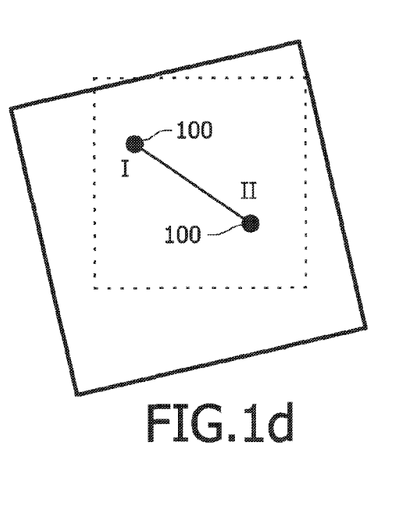

The software freezes the position and orientation of the markers (with respect to each other) at the centre of the monitor screen in every frame of the run and matches the position of the markers to the positions in the first frame. Referring to FIG. 1 of the drawings, the three basic operations to realise this image registration are: translation, rotation and stretching. More specifically, markers 100 are automatically extracted in frames I and II (FIG. 1a), and a translation step is then performed to translate the position of the markers 100 in frame II to correspond with that of the markers 100 in frame I (FIG. 1b). Next, frame II is rotated so that the respective markers in frames I and II are aligned (FIG. 1c) and fram II is expanded so as to "stretch" the position of the markers 100 therein to correspond with that of frame I (FIG. 1d).

The direct environment that has a fixed position with respect to the markers 100, including the stent, is frozen as well. The environment further away, however, is moving from frame to frame due to the motion of the heart and respiration. Averaging of the frozen frames leads thus to a much enhanced contrast of the environment of the markers, and therefore of the stent, whereas all structures and noise of surrounding areas are smoothed out with a subsequent loss of contrast.

The known method described above results in a static view of the enhanced stent against a blurred background, and this blurring of the background is essentially possible due to the cardiac motion of the stent, with respect to the static background. This implies that for static stents (e.g. carotid stents) this method is not so effective and does not result in such nicely blurred backgrounds in images, relative to that which can be achieved for moving stents. Another disadvantage is that the stent 200 is represented in a static view, whereas it may be desirable, at least sometimes, to view the enhanced stent in motion. This would provide an improvement relative to current single projection views, which have to be repeated several times to get information on the complete deployment state of the stent.

Thus, in accordance with the invention, apparent motion of an otherwise stationary (e.g. carotid) stent is introduced by deliberately moving the detector relative to the stent, for example, by zooming in on the stent. Then, applying the above-described stent enhancement method on the thus-acquired sequence results in the desired enhanced view of the stent on suitably blurred background. Of course, this relative movement of the detector relative to the stent (e.g. zooming in) may also be used in respect of moving stents to further improve the enhancement thereof.

As an alternative to zooming in, another way of introducing the required motion of the detector relative to the stent is to rotate the detector around the patient (and, therefore, the stent). Applying the above-mentioned enhancement method now, while using recursive temporal filtering, will once again result in an enhanced view of the stent against a blurred background, but this time viewed in all the projections induced by the detector motion.

Of course, detector motion is not limited to rotation and zooming relative to the stent, and other types of motion would also work, although rotation and zooming have been found to be particularly advantageous in achieving the object of the invention.

Figure 2A:
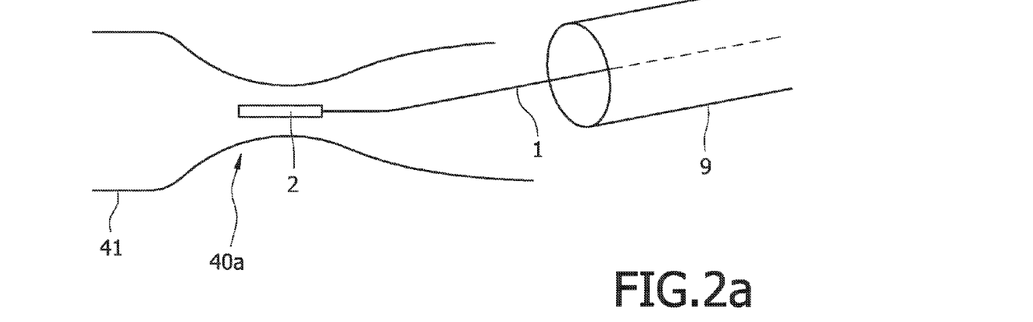
FIGS. 2a to 2f illustrate schematically the principal stages of an angioplasty.

An embodiment of the invention will now be described in more detail relative to a medical intervention known as an angioplasty. Referring to FIGS. 2a to 2f of the drawings, such a medical intervention includes stages of:

Referring to FIG. 2a, introduction in the artery 41, using a catheter 9, of a thin guide-wire 1 that extends beyond the extremity of the catheter 9, and passes through the small lumen of the artery portion 40a at the location of the stenosis.

Figure 2B:
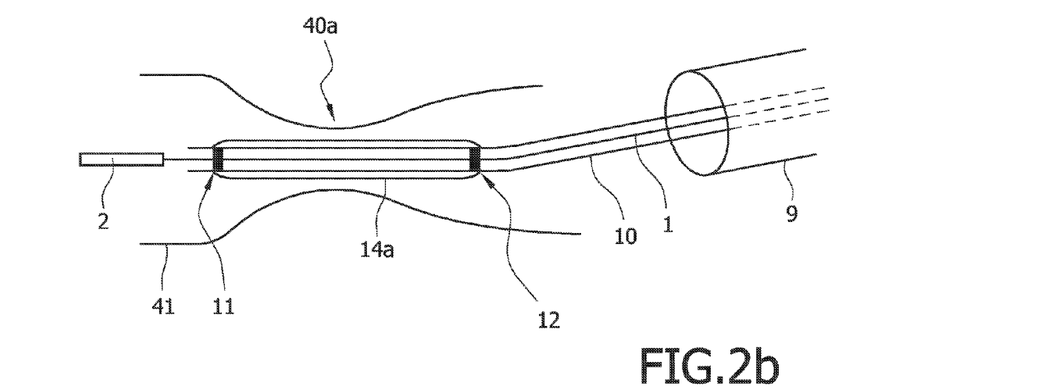

Referring to FIG. 2b, introduction of a monorail 10, which is guided by said guide-wire 1 that passes through the opening 3 of the monorail 10, and which has a first balloon 14a wrapped around its extremity, without stent; and positioning said first balloon 14a in the artery portion 40a at the stenosis location.

Figure 2C:
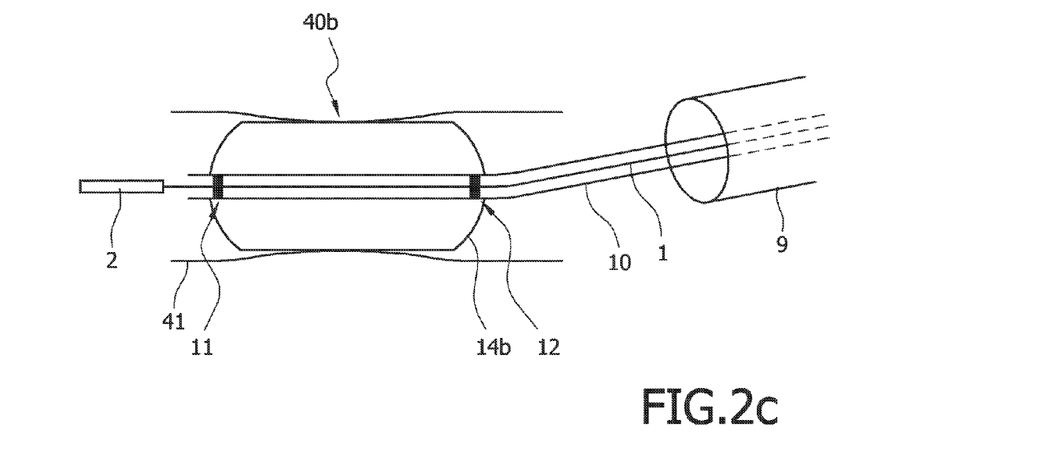

Referring to FIG. 2c, inflation of this first balloon 14a, which becomes the inflated balloon 14b, for expanding the narrow lumen 40a of the artery 41 at the location of the stenosis to become the enlarged portion 40b of the artery 41; then, the removal of the first balloon 14b with the first monorail 10.

Referring to FIG. 2d, again using the catheter 9 and the thin guide-wire 1, introduction of a second monorail 20 with a second balloon 24a wrapped around its extremity, and with a stent 25a around said second balloon 24a; and positioning said second balloon with the stent at the location of the stenosis in the previously expanded lumen 40b of the artery 41.

Figure 2D:
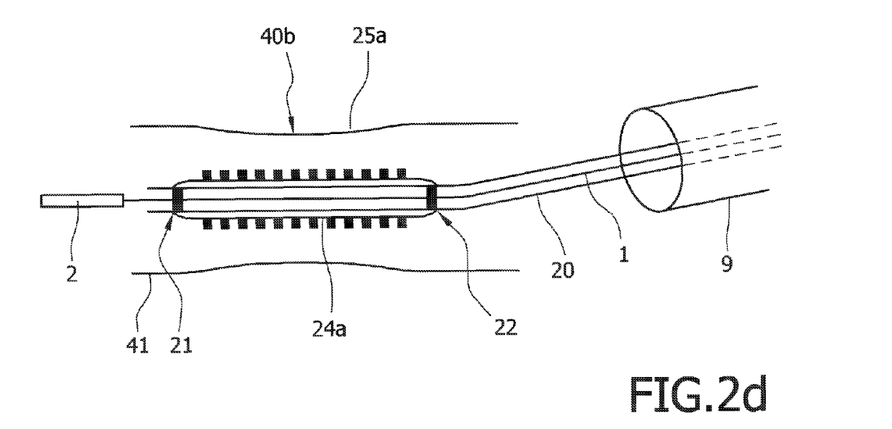
Figure 2E:
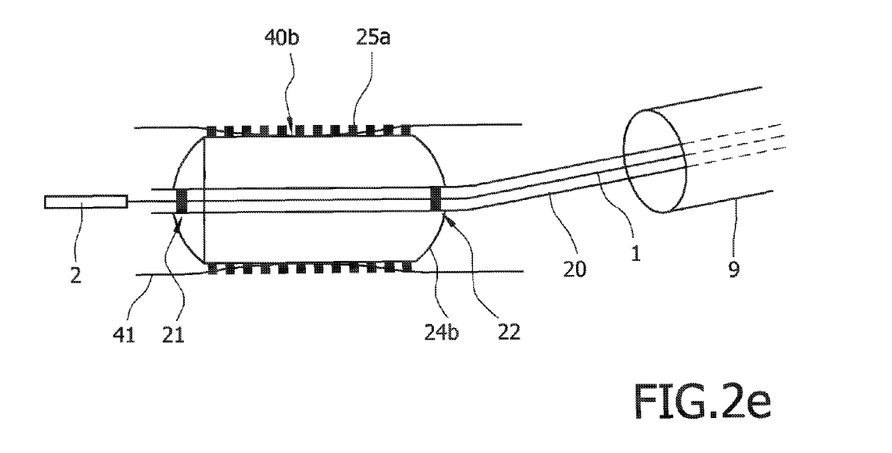

Referring to FIG. 2e, inflation of the second balloon 24a to become the inflated balloon 24b in order to expand the coil forming the stent 25a, which becomes the expanded stent 25b embedded in the artery wall.

Figure 2F:
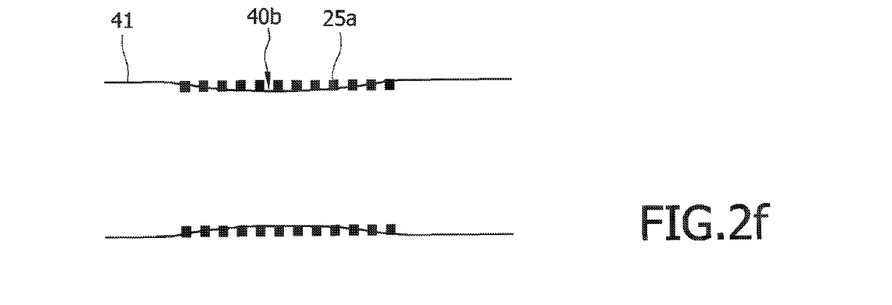

Referring to FIG. 2f, considering the expanded stent 25b as a permanent implant, removing the second balloon 24b, the second monorail 20, the guide-wire 1 and the catheter 9.

This type of medical intervention can be difficult to carry out as a result of badly contrasted images, and some stages of the intervention are critical, so that checking actions have to be performed during these stages. For example, between stages d) and e), it is critical to check whether the stent 25a is accurately positioned with respect to the expanded lumen 40b of the artery 41.

Figure 4:
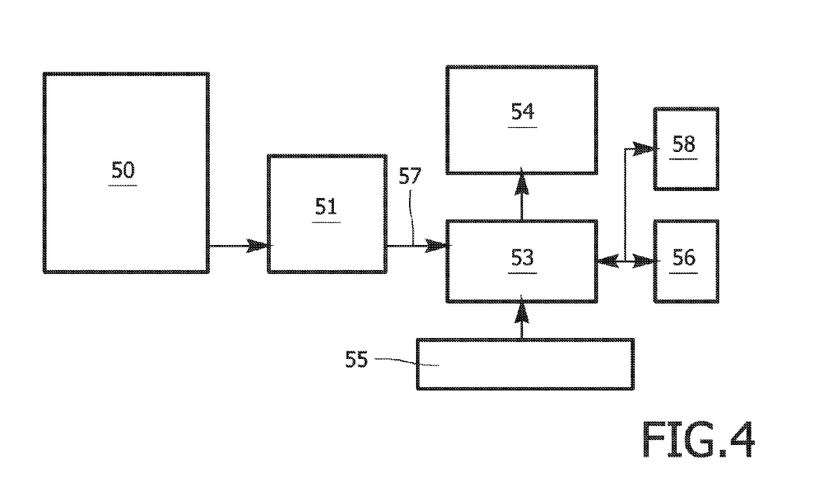
FIG. 4 is a schematic functional block diagram of a medical examination apparatus for use in a method according to an exemplary embodiment of the present invention.

Referring to FIG. 4 of the drawings, suitable medical examination apparatus 50 for use in a method according to the invention may comprise means 51 for acquiring digital image data of a sequence of images, which means are coupled to a medical viewing system 53 according to an exemplary embodiment of the present invention for processing the digital image data. The medical viewing system is generally used in or near the intervention room for processing real time images, but it may equally be used on stored medical images, for example for estimating medical parameters. The system for processing the data of the stored images is known as the medical viewing station. The medical examination apparatus provides the image data by connection 57 to the system 53. The system provides processed image data to display means and/or storage means. In the special case where the relative motion is introduced by rotation of the detector relative to the tool, the rotating tool may be displayed on the original image thereof to give a normal view of the enhanced tool. In any event, the display means 54 may be a screen. The storage means may be a memory MEM of the system 53, or may alternatively comprise external storage means. This image viewing system 53 may comprise a suitably programmed computer, or a special purpose processor having circuit means such as LUTs, Memories, Filters, Logic Operators, that are arranged to perform the functions of the enhancement method. The system 53 may also comprise a keyboard 55 and a mouse 56. Icons may be provided on the screen to be activated by mouse-clicks, or special pushbuttons may be provided on the system, to constitute control means 58 for the user to start, control the duration or stop the processing means as required. The control means may also be arranged and configured to allow the user to control and adjust the playback speed of the sequence of enhanced images, as required.

Figure 3:
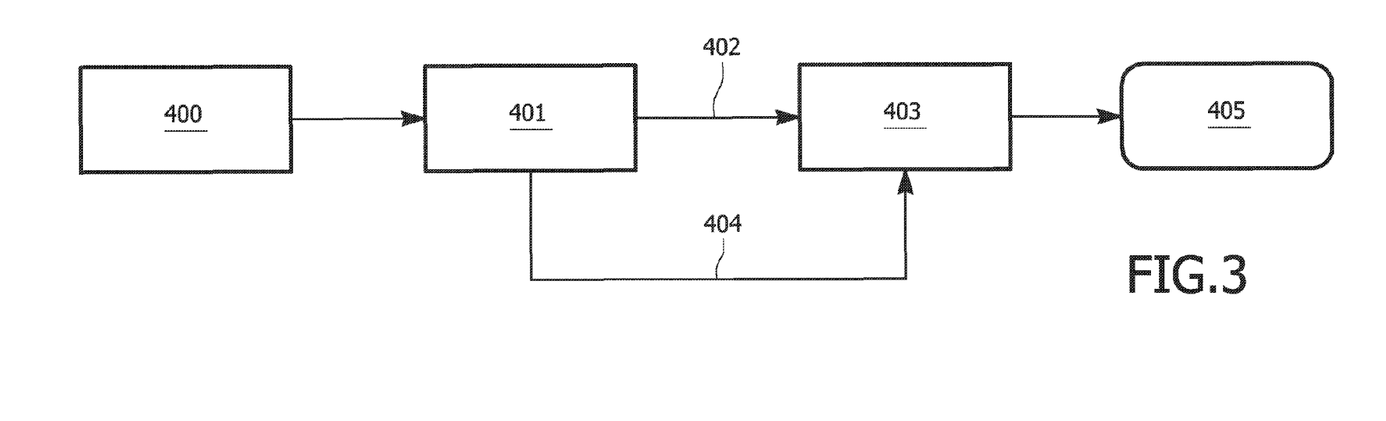
FIG. 3 is a schematic block diagram of the principal steps of a method according to an exemplary embodiment of the present invention.

Thus, referring to FIG. 3 of the drawings, once the second balloon 24a within the stent 25a has been positioned at the location of the stenosis in the previously expanded lumen 40b of the artery 41 (step 400), the medical examination apparatus is employed by the user to carry out the required checking action. First, detector motion is introduced (at step 401) relative to the stent, for example, by zooming in on the region of interest containing the stent or by rotating the detector around the patient (and, therefore, the stent) to capture image data 402 of a sequence of images of the stent, and this image data 402 is passed to image processing means 403 for enhancement of the stent within the captured images. Additionally, geometry system data 404 is also passed to the image processing means means 403. The image processing means 403 includes enhancement means for enhancing the view of the stent within the sequence of images, and the enhanced image sequence 405 is output.

Figure 5:
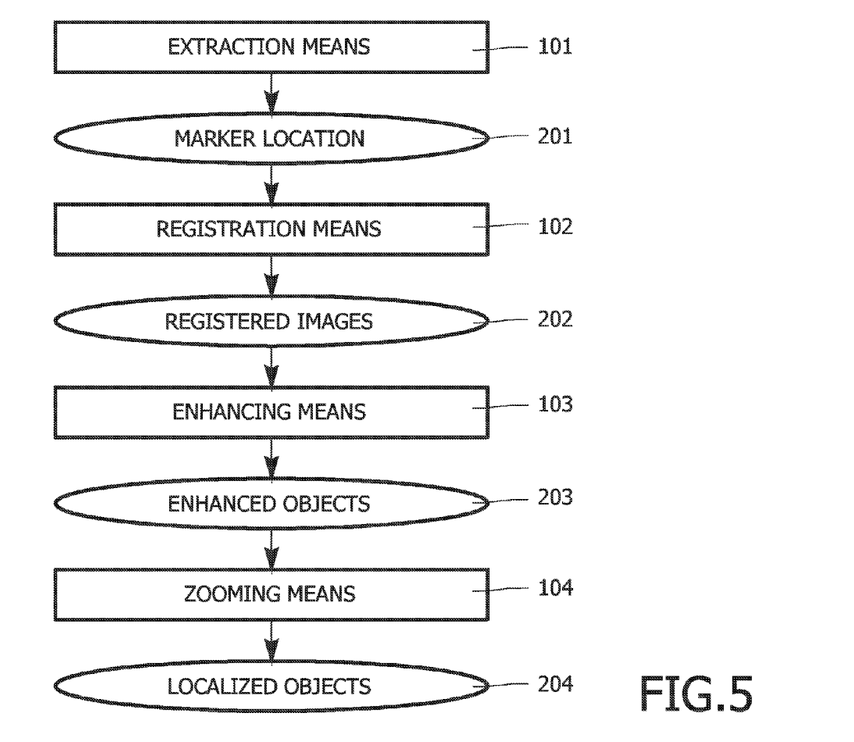
FIG. 5 is a schematic functional block diagram of an enhancement means for use in a method according to an exemplary embodiment of the present invention.

In more detail, and referring to FIG. 5, the image processing means 403 include extracting means 101 that solves the problems of automatically and accurately localized specific features in the sequence. Once the specific feature location 201 has been determined by the automatic extracting means 101, registering means 102 provides registered sequence images 202, based on the specific feature location 201. Then, enhancing means 103 yields images 203 with the enhanced tool.

Figure 6:
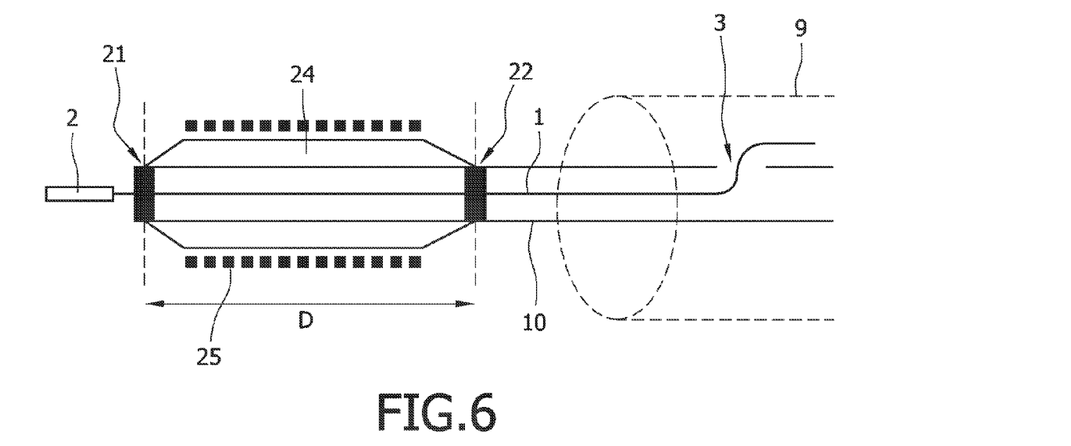
FIG. 6 illustrates schematically a device constituted by a catheter, a guide-wire and a monorail with a balloon and a stent wrapped around it.

Referring additionally to FIG. 6 of the drawings, the extracting means 101 is arranged and configured to automatically and accurately extract specific features among which a feature called guide-wire tip 2 located at the extremity of the thin guide-wire 1 guiding the monorail 10; and/or at least one feature called a balloon-marker 11, 12 or 21, 22 located respectively on the monorail 10 at a given position with respect to the balloon respectively 14a, 24a; preferably there are two balloon-markers disposed at each extremity of the balloon. The guide-wire tip 2 does not belong to either the artery walls or the stent 25, since it belongs to the guide-wire 1. Also, the balloon-markers 11, 12, 21, 22 belong neither to the vessel walls nor to the stent 25 since they belong to the monorail 10. These markers have a specific easily recognizable shape, and are made of a material highly contrasted in the images. Hence they are easy to extract. The system processing means 102, 103, 104 permit of accurately deriving the location of the balloons, since the balloons have specific locations with respect to the balloon-markers. Also, the stents are accurately localized, since the stents have specific locations with respect to the balloon-markers though said stents are not attached to said balloon-markers.

Figure 7:
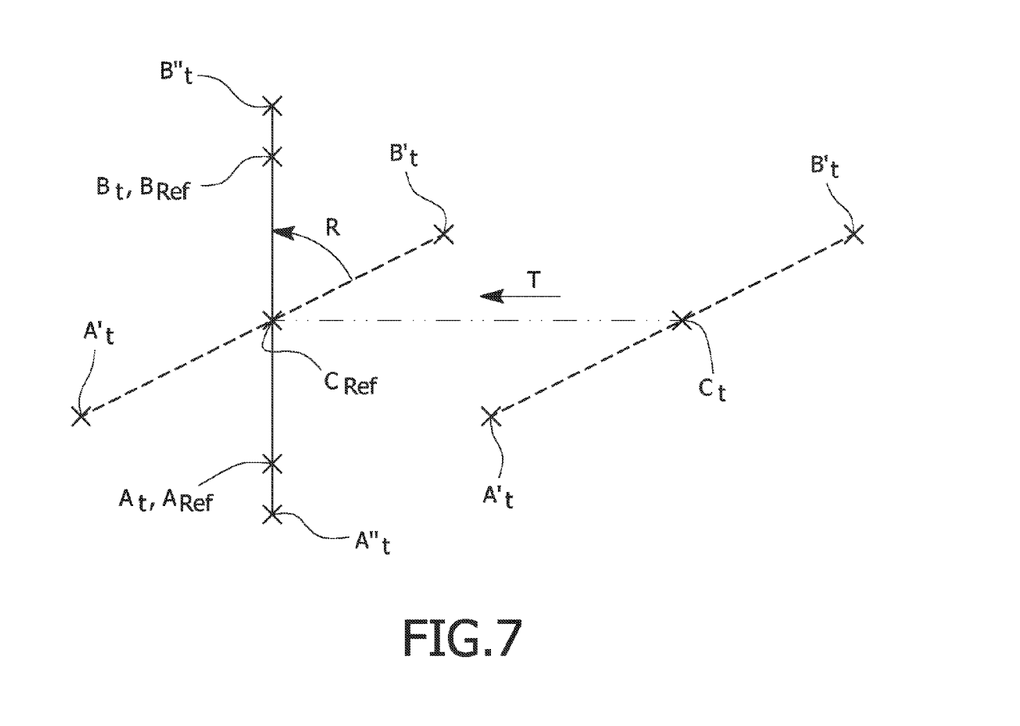
FIG. 7 illustrates the step of marker registration.

Referring to FIG. 7, for instance two markers $A_{Ref}$, $B_{Ref}$ have been detected in an image of the sequence, called image of reference, which may be the image at starting time. The markers $A_{Ref}$, $B_{Ref}$ may be selected by automatic means. They are extracted using extracting means 101 of the system. Then, registering means 102 of the system, using the marker location information $A_{Ref}$, $B_{Ref}$ in the reference image and corresponding extraced markers $A'_t$, $B'_t$ in a current image of the sequence, are operated for automatically registering the current image on the reference image. This operation is performed by matching the markers of the current image to the corresponding markers of the reference image, comprising possible geometrical operations including: A translation T to match a centroid $C_t$ of the segment $A'_t B'_t$ of the current image with a centroid $C_{Ref}$ of the segment $A_{Ref} B_{Ref}$ of the reference image; a rotation R to match the direction of the segment $A'_t B'_t$ of the current image with the direction of the segment $A_{Ref} B_{Ref}$ of the reference image, resulting in a segment $A''_t B''_t$; and a dilation $\Delta$ for matching the length of the resulting segment $A'_t B'_t$ with the length of the segment $A_{Ref} B_{Ref}$ of the reference image, resulting in the registered segment $A_t B_t$ for the registered current image. Such operations of translation T, rotation R and dilation $\Delta$ are defined between the images of the sequence and the reference image, resulting in the registration of the whole sequence. This operation of registration is not necessarily performed on all the points of the images. Zones of interest comprising the markers may be delimited. This operation of registration permits of minimizing the effect of respective movements of the objects of interest, such as vessels, guide-wire, balloons and stent, with respect to a predetermined image referential. In the registered images, the user can easily perform zooming Z on the objects of interest. Preferably, two markers, or more, are used for better registration.

In the registered sequence, an object of interest, such as stent, can be enhanced by the enhancing means 103. For this operation, the shape and dimension of the stent is a-priori knowledge that can be stored in memory means of the system. The boundaries of the stent are substantially parallel to the segment formed by the balloon-markers, and at a distance from this segment that can be derived from the a-priori knowledge. So, these boundaries are detected, extracted and enhanced by the enhancing means 103 of the system. Also, the artery walls can be detected, extracted and enhanced by the enhancing means 103 in a similar manner.

The registered images are preferably filtered for minimizing noise. The system enhancing means 103 may comprise noise filter means. In an example, the registered images are integrated by averaging means applied to the intensity of the points. By this operation, the details of objects, such as vessels, which are in time concordance, are enhanced while the details of the background which are not in time concordance, are minimized. The registered images are also preferably submitted to spatial background subtraction means of the enhancing means 103. Background substraction means permits of eliminating large contrasted zones and permits of again enhancing the objects of interest.

Referring back to FIG. 3, in the case that the relative detection made is achieved by zooming-in on the stent, the image processing performed by the means 403 can be interpreted as a first iteration of the so-called "super-resolution" algorithm, such as that described by Irani and Peleg in "Improving Resolution by Image Registration", CVGIP— Graphic Models and Image Processing, 1991 which is an algorithm for increasing the spacial resolution of the object. By applying this technique, image quality of the stent can be leveraged to "any" desired resolution, provided that there are enough frames in the dynamic stent sequence 402. Intuitively, this can be interpreted as a digitally extended "virtual" zooming-in of the detection with respect to the stent.

In the specific case, where the relative motion is introduced by rotation of the detector relative to the tool, the enhancement means preferably employs temporal recursive filtering means to produce an enhanced image of the tool. Furthermore, symmetrical temporal integration may be applied to images that are exactly 180 degrees apart (and, therefore, contain the same projection of the tool) so as to improve the enhancement result. The window for temporal integration may be adapted to the rotation speed of the detector.

Although an embodiment of the present invention has been described above in relation to a stationary medical intervention, it is equally applicable to non-stationary (e.g. cardio) applications, and the present invention is not necessarily intended to be limited in this regard.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method of medical imaging comprising:
   at least one of moving and positioning a tool in a body organ using a tool support;
   acquiring a sequence of 2D fluoroscopic images of said tool with an image detector;
   during the acquiring step, moving said image detector relative to said tool such that the fluoroscopic images of the sequence are acquired at least one of from different directions and with different levels of zoom;
   automatically extracting markers attached to said tool support and yielding marker location information;
   at least one of rotating, translating, and scaling the fluoroscopic images of the sequence to bring the markers into registration in the fluoroscopic images of the sequence, background portions of the registered images being different in different images due to being acquired at least one of from different directions and with different levels of zoom;
   deriving tool location information from said marker location information in the registered images of the sequence; and
   integrating the registered images of said sequence to coherently sum portions of the image including the tool to improve the visibility of said tool and sum the background portions of the images to blur the background such that the visibility of the tool is enhanced relative to the background.

2. The method according to claim 1, wherein said movement of the detector relative to the tool is simulated by zooming in on the tool.

3. The method according to claim 1, wherein said movement of the detector relative to the tool is effected by rotating the detector relative to the tool.

4. The method according to claim 3, wherein said detector is rotated substantially about a tool axis.

5. The method according to claim 3, further including:
   temporal recursive filtering during the integrating step to produce an image of a rotating enhanced tool.

6. The method according to claim 3, wherein the integrating step includes symmetrical temporal integration of images of the sequence that are acquired 180 degrees offset from each other.

7. The method according to claim 6, further including:
   adapting a window for the symmetrical temporal integration to a rotation speed of the detector.

8. The method according to claim 1, wherein the tool is stationary relative to the body organ during acquisition of the sequence of images.

9. The method according to claim 1, further comprising:
   receiving system geometry data indicative of detector movement relative to the tool.

10. A medical imaging system comprising:
    a fluoroscopic image detector which acquires a sequence of fluoroscopic images of a surgical tool which is instrumented with markers that are visible in the fluoroscopic images during a medical intervention, the detector moving relative to said tool during acquisition of said sequence of fluoroscopic images;
    a processor programmed to:
      receive the sequence of fluoroscopic images from the detector;
      identify the markers in each fluoroscopic image;
      at least one of translate, rotate, and scale the fluoroscopic images to bring the markers in each fluoroscopic image into alignment such that the tool and the markers, are aligned and background anatomy is misaligned in each image of the sequence of fluoroscopic images due to the motion of the fluoroscopic image detector;

combine each fluoroscopic image with previous fluoroscopic images of the sequence of fluoroscopic images such that the aligned tool and markers sum to enhance the tool and the markers and the background anatomy in the image is deemphasized due to the moving of the detector; and a display which displays the combined fluoroscopic images.

11. The system according to claim 10, wherein the processor is further programmed to:

adjust a playback speed of the sequence of fluoroscopic images during display thereof.

12. A medical image viewing method comprising:

with a fluoroscopic detector, acquiring a sequence of fluoroscopic images of a region of a patient in which region a tool is positioned by a tool support during a medical intervention;

moving the fluoroscopic detector relative to the tool during the acquisition of the sequence of fluoroscopic images;

in each fluoroscopic image of the sequence of fluoroscopic images, automatically extracting at least one marker attached to the tool support;

with the processor, registering the marker with a common location in each fluoroscopic image of the sequence of fluoroscopic images such that the tool is in the same location in each of the fluoroscopic images of the sequence, the moving of the fluoroscopic detector being performed such that background anatomy of the patient around the tool varies in each fluoroscopic image of the sequence of fluoroscopic images;

with the processor, combining a current fluoroscopic image of the sequence of fluoroscopic images with preceding fluoroscopic images of the sequence such that combining a plurality of images of the tool in the common location of each of the images enhances the visibility of the tool relative to the background anatomy of the patient around the tool which differs in each of the images; and displaying the current fluoroscopic image and a display device.

13. The method according to claim 12, wherein the fluoroscopic images are two-dimensional in projection images.

14. The method according to claim 12, wherein the fluoroscopic detector moves toward and away from the tool.

15. The method according to claim 12, wherein at least two markers are attached to the tool support and registering the markers includes at least one of scaling, rotating, and translating the fluoroscopic images to bring the markers into registration.

* * * * *